United States Patent
Bagha et al.

(10) Patent No.: US 8,900,153 B2
(45) Date of Patent: Dec. 2, 2014

(54) AMBULATORY PATIENT MONITORING APPARATUS, SYSTEM AND METHOD

(75) Inventors: Merat Bagha, Portland, OR (US); Pedro Mateo Riobo Aboy, Beaverton, OR (US)

(73) Assignee: Mortara Instrument, Inc., Milwaukee, WI (US)

( * ) Notice: Subject to any disclaimer, the term of this patent is extended or adjusted under 35 U.S.C. 154(b) by 1768 days.

(21) Appl. No.: 12/052,674

(22) Filed: Mar. 20, 2008

(65) Prior Publication Data

US 2008/0234587 A1 Sep. 25, 2008

Related U.S. Application Data

(60) Provisional application No. 60/895,898, filed on Mar. 20, 2007.

(51) Int. Cl.

| | |
|---|---|
| *A61B 5/02* | (2006.01) |
| *A61B 5/0205* | (2006.01) |
| *A61B 5/00* | (2006.01) |
| *A61B 5/021* | (2006.01) |
| *A61B 5/0402* | (2006.01) |
| *A61B 5/11* | (2006.01) |
| *A61B 5/145* | (2006.01) |

(52) U.S. Cl.
CPC ............. *A61B 5/0205* (2013.01); *A61B 5/7475* (2013.01); *A61B 5/021* (2013.01); *A61B 5/0402* (2013.01); *A61B 5/11* (2013.01); *A61B 5/145* (2013.01)
USPC .............................. 600/483; 600/485; 600/500

(58) Field of Classification Search
None
See application file for complete search history.

(56) References Cited

U.S. PATENT DOCUMENTS

| | | |
|---|---|---|
| 4,576,180 A | 3/1986 | Taheri |
| 4,706,684 A | 11/1987 | Sorensen et al. |
| 4,830,018 A | 5/1989 | Treatch |
| 4,889,132 A | 12/1989 | Hutcheson et al. |
| 4,967,756 A | 11/1990 | Hewitt |
| 5,778,879 A * | 7/1998 | Ota et al. ...................... 600/485 |
| 6,251,080 B1 | 6/2001 | Henkin et al. |
| 7,697,983 B1 * | 4/2010 | Oza ................................... 607/5 |
| 2006/0235316 A1 | 10/2006 | Ungless et al. |
| 2007/0055115 A1 * | 3/2007 | Kwok et al. .................. 600/300 |
| 2007/0244721 A1 | 10/2007 | Sackner-Bernstein et al. |

FOREIGN PATENT DOCUMENTS

GB 2454705 A * 5/2009

OTHER PUBLICATIONS

Deckers (Br. Heart J. 1990. vol. 64: pp. 376-380).*
McGovern et al (Chest, 1996. vol. 109, pp. 1151-155).*
Mini Mitter; Actical—Physical Activity and Caloric Expenditure Monitoring System (brochure), Mini-Mitter Part No. 900-164-00/REV Mar. 2004; USA.

* cited by examiner

*Primary Examiner* — Celine Qian
(74) *Attorney, Agent, or Firm* — Mateo Aboy; Aboy & Associates PC

(57) ABSTRACT

A patient monitoring device that combines physiological data collection with actigraphy data collection and associates the physiological data with synchronous actigraphy data. A method for processing actigraphy data by calculating absolute difference vectors of actigraphy signal vectors.

8 Claims, 3 Drawing Sheets

AMBULATORY PATIENT MONITORING APPARATUS, SYSTEM AND METHOD

CROSS-REFERENCE

This application claims the benefit of U.S. Provisional Patent Application No. 60/895,898 filed on 2007 Mar. 20 by the present inventors, which is incorporated by reference.

BACKGROUND OF THE INVENTION

1. Field of the Invention

The present invention relates to automated non-invasive patient monitoring devices. Specifically, it relates to non-invasive patient monitoring devices which incorporate integrated actigraphy as a means for synchronizing physiological measurements with activity/rest cycles.

2. Description of the Related Art

Automated non-invasive patient monitoring devices such as the devices used in ambulatory blood pressure monitoring are well-known and commercially available. These devices enable clinicians to monitor a patient's physiological data during regular daily activity in the patient's everyday environment.

The human circadian or diurnal rhythm, including day-night patterns of vital signs, has a fundamental role in both in the proper diagnosis and treatment of patients. For example, almost all cardiovascular system functions, including heart rate, blood pressure, and blood flow exhibit circadian variability. Such rhythms in the physiological status of the cardiovascular system along with temporal patterns in the occurrence and intensity of environmental triggers of disease give rise to predictable-in-time differences in the susceptibility/resistance of persons to serious cardiovascular events such as heart attacks and strokes. As such, it is extremely valuable to have physiological data obtained on a patient correlated to their exact circadian rhythm including day-night patterns.

Existing physiological data monitors, whether home or clinic patient monitors as well as ambulatory patient monitors (see U.S. Pat. Nos. 4,830,018, 4,706,684, 6,251,080, 4,576,180, 4,967,756, 4,889,132), do not directly monitor and factor in the circadian or diurnal rhythm of a patient or include an integrated actigrapher. As such, they miss a critical component of the patient's conditions that would aid in better assessing the patient and developing a course of therapy optimized for that patient's conditions. Further, a comparison of two or more extended term (e.g., 24 hour) diagnostic data sets for a patient—such as that of a pre- and post-medication treatment—often fails to take into account subtle differences in the patient's circadian or diurnal rhythm. Any consideration for circadian rhythm variability is typically dependent on incomplete or imprecise statements or diaries from healthcare providers or patients which can drastically skew the results of any analysis or comparison.

Integrated actigraphy is critical to determine the patient's activity/rest patterns and to make possible automatic synchronization of pre-treatment and post-treatment recordings in order to evaluate the efficacy of treatment such as antihypertensive therapy. Integrated actigraphy is also critical in order to synchronize physiological recordings from different patients enrolled in clinical studies and clinical trials since each individual has different activity/rest patterns (for instance, patients wake up a different times).

Actigraphy has been recognized in prior art to identify circadian rhythms, sleep patterns, pharmacological treatment of hypertension, resynchronization of body clocks, etc. However, such prior art does not include the collection of physiological data over an extended basis in conjunction with actigraphy. As such, this prior art does not provide the ability to combine extended monitoring of physiological data along with actigraphy which are critical to correlating and analyzing patient conditions in response to circadian rhythm variations including asleep/awake patterns.

BRIEF DESCRIPTION OF THE SEVERAL VIEWS OF THE DRAWING(S)

DETAILED DESCRIPTION OF THE INVENTION

Figure 1:
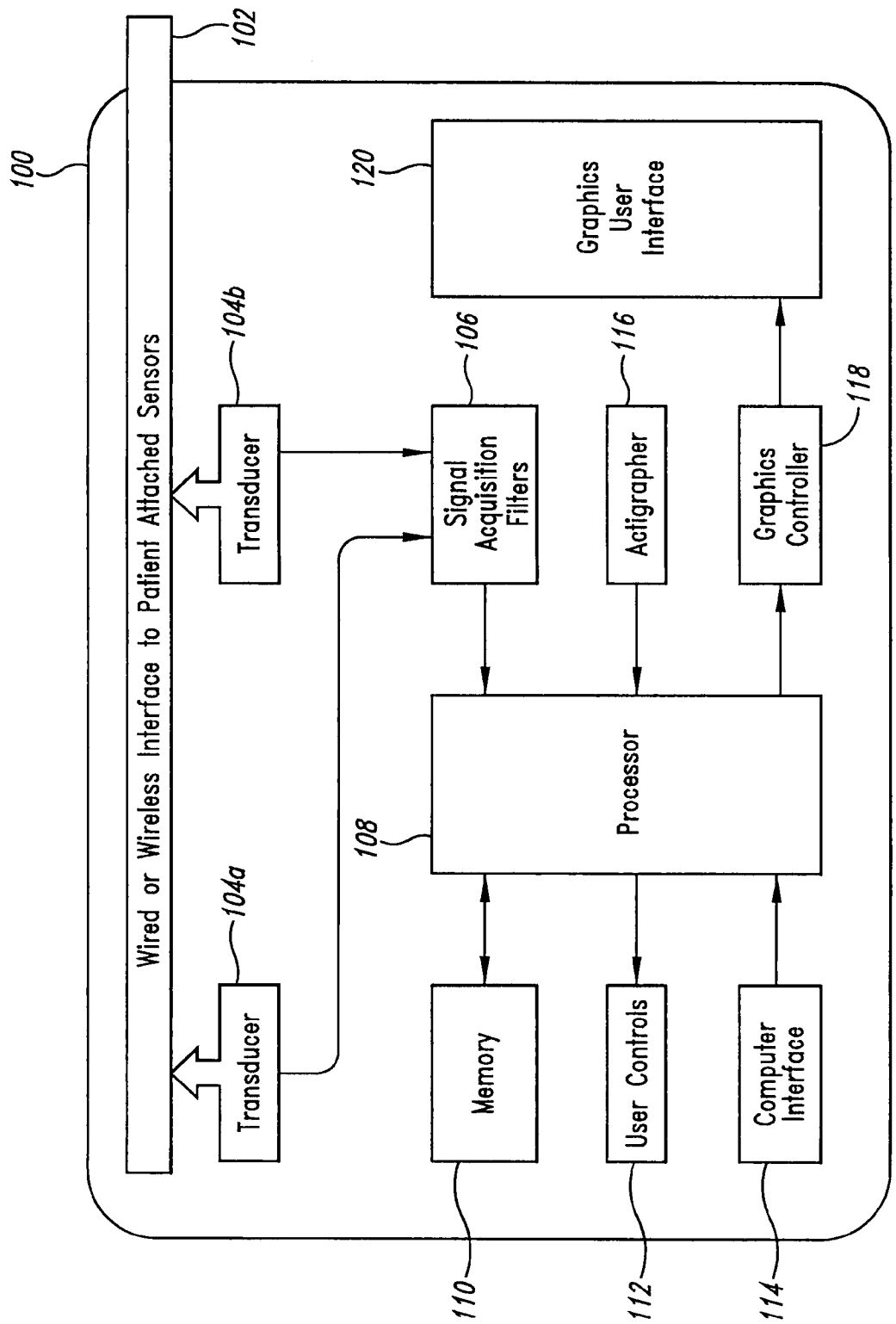
FIG. 1 shows a block diagram of an embodiment of a patient monitoring device with integrated actigraphy.

FIG. 1 shows a block diagram of a patient monitoring device 100 with actigraphy. The patient monitoring device 100 is configured to receive physiological sensor data from sensors (not shown) attached to a patient wearing the monitoring device 100, associate the physiological sensor data with synchronous actigraphy data and store the associated physiological sensor and actigraphy data. The stored physiological sensor data and the associated actigraphy data can later be retrieved for analysis. Examples of sensors that may be used with the patient monitoring device 100 include, without limitation, blood pressure monitors, body temperature thermometers, electro-cardiograph electrodes, blood oxygen monitors and microphones.

The patient monitoring device 100 includes a sensor interface 102, a processor 108, a memory 110, an actigrapher 116 and a computer interface 114. The sensor interface 102 is configured to provide a signal path to the sensors. In some embodiments the sensor interface 102 is configured to provide a wireless signal path. In other embodiments, the sensor interface 102 is configured to provide a wireline signal path. The processor 108 is coupled with the sensor interface 102 and configured to receive physiological sensor data from the sensors. The processor 108 is coupled with the actigrapher 116 and configured to receive actigraphy data from the actigrapher 116. The processor 108 is configured to associate physiological sensor data with actigraphy data and store the sensor and actigraphy data in the memory 110. The computer interface 114 is configured to transfer stored physiological sensor data and associated actigraphy data from the patient monitoring device 100 to an external computer or storage device, where it can later be analyzed by medical professionals. In some embodiments, the computer interface 114 is configured to transfer instructions from the external computer to the patient monitoring device 100.

The actigrapher 116 provides actigraphy data. Actigraphy data indicates a level of activity of the patient wearing the patient monitoring device 100. In some embodiments the actigrapher 116 measures activity level with a 3-axis accelerometer, in which case, the actigraphy data includes measurements of acceleration. In other embodiments, the actigrapher 116 measures activity level with a gyroscope, and in yet other embodiments, with a tilt/inclination sensor.

In some embodiments, the patient monitoring device 100 includes transducers 104 and signal acquisition filters 106. The transducers 104 are configured to receive physiological sensor data from the sensors through the sensor interface 102 and to convert the physiological sensor data from analog to digital. The signal acquisition filters 106 are configured to receive physiological sensor data from the transducers 104, to filter out noise and extraneous signals, and to pass the filtered physiological sensor data to the processor 108. In other embodiments, the functions provided by the transducers 104 and signal acquisition filters 106 are provided by devices external to the patient monitoring device 100.

In some embodiments, the patient monitoring device 100 includes user controls 112. The user controls 112 are configured to accept instructions from a user and transfer the instructions to the processor 108. Other embodiments omit user controls 112 and instead receive instructions during manufacture of the patient monitoring device 100 or receive instructions through the computer interface 114.

In some embodiments, the patient monitor includes a graphics controller 118 and a graphics user interface 120. The graphics user interface 120 is configured to display information retrieved from the memory 110 for the user to view. The graphics controller 118 is configured to render the information retrieved from the memory 110 into a format usable by the graphics user interface 120.

Figure 2:
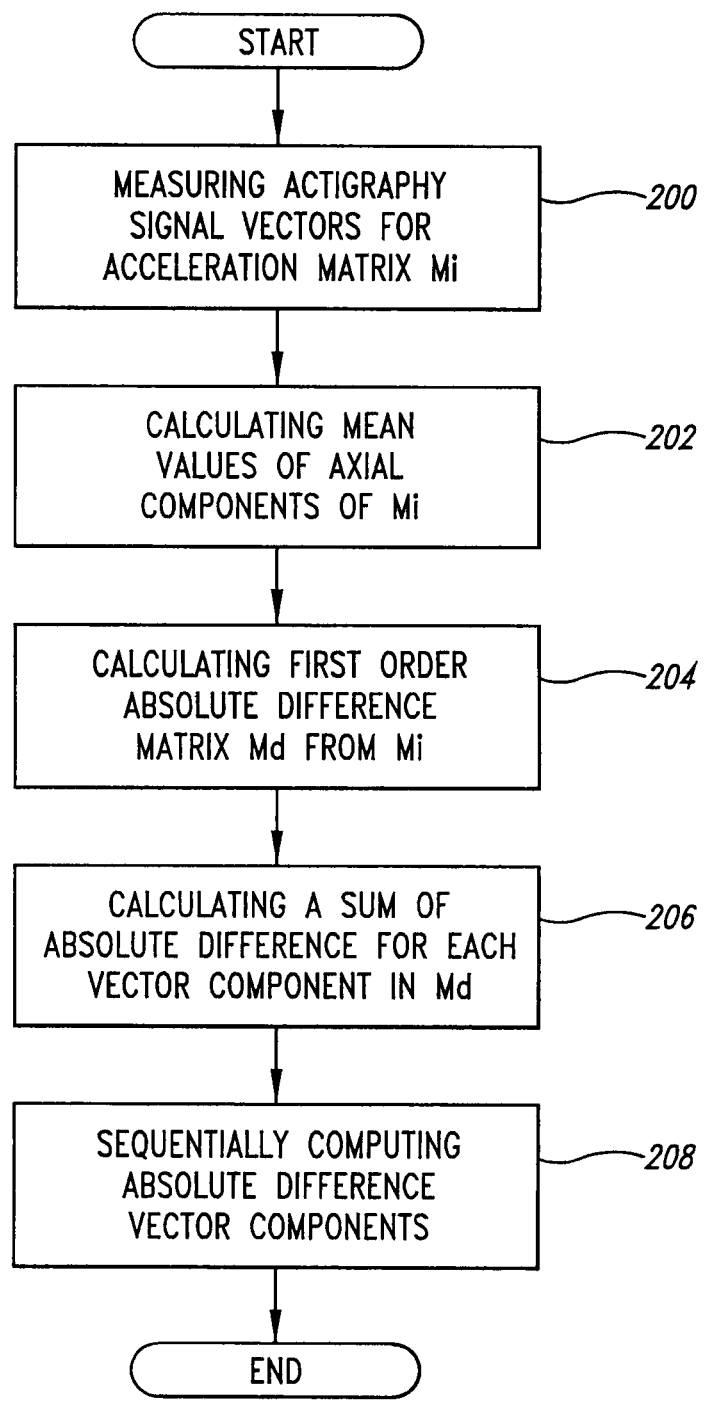
FIG. 2 shows a flow chart of a method for processing actigraphy data.

FIG. 2 shows a flow chart of a method for processing actigraphy data. Some embodiments of the patient monitoring device 100 use this method. Other embodiments may use other methods.

Step 200 comprises measuring N number of actigraphy signal vectors during a sample window. The number N is equivalent to $f_s$ times $w_l$, where $f_s$ is the sample frequency and $w_l$ is the time width of the sample window. Each actigraphy signal vector represents actigraphy data taken during a particular sample. Each actigraphy signal vector has 3 components, one for each of 3 spatial axes (x, y, z). Each component represents a measured amount of acceleration along the respective axis during the particular sample. The actigraphy signal vectors are stored in an acceleration matrix $M_i$, as shown in Equation 1:

$$M_i = (x, y, z) \tag{1}$$

The acceleration matrix $M_i$ comprises N number of 3 dimensional actigraphy signal vectors. In some embodiments, the actigrapher 116 generates the actigraphy signal vectors.

Step 202 comprises calculating mean values for each of the axial components of the acceleration matrix $M_i$. The mean values are stored together as a mean acceleration vector $m_{dc}$, as shown in Equation 2:

$$m_{dc} = (x, y, z) \tag{2}$$

Step 204 comprises calculating a first order absolute difference vector $(x^d, y^d, z^d)$ for each of N actigraphy signal vectors in the acceleration matrix $M_i$. This is done by calculating for each of the N actigraphy signal vectors an absolute difference for each actigraphy signal vector component (x, y, z). Using k as an index of samples 1 to N, the absolute difference for each component of actigraphy signal vector k+1 is equal to the absolute value of the difference between the value of the vector component in sample k+1 minus the value of the vector component in sample k. The absolute difference vectors $(x^d, y^d, z^d)$ for the N actigraphy signal vectors are stored in an absolute difference matrix $M_d$. Step 204 is performed in accordance with Equations 3-6:

$$x_{k+1}^d = |x_{k+1} - x_k| \tag{3}$$

$$y_{k+1}^d = |y_{k+1} - y_k| \tag{4}$$

$$z_{k+1}^d = |z_{k+1} - z_k| \tag{5}$$

$$M_d = (\{x_{k+1}^d\}_{k=1}^N, \{y_{k+1}^d\}_{k=1}^N, \{z_{k+1}^d\}_{k=1}^N) \tag{6}$$

Step 206 comprises calculating a sum of absolute differences for each vector component in the absolute difference matrix $M_d$. The results are stored in an absolute difference vector $m_1$. Step 206 is performed in accordance with Equations 7-8:

$$\bar{x}_1 = \sum_{k=1}^N x_k^d, \bar{y}_1 = \sum_{k=1}^N y_k^d, \bar{z}_1 = \sum_{k=1}^N z_k^d \tag{7}$$

$$m_1 = (\bar{x}_1, \bar{y}_1, \bar{z}_1) \tag{8}$$

Step 208 comprises sequentially compiling absolute difference vectors components calculated during sequential sample windows and storing the results in a final matrix M. Step 208 is performed in accordance with Equation 9:

$$M = \{m_k\}_{k=1}^J = \{(\bar{x}_1, \bar{y}_1, \bar{z}_1)\}_{k=1}^J \tag{9}$$

where J is a duration in seconds of a recording session. Final matrix M can be associated with physiological data taking during the same time. Each biometric data point can be associated with a synchronous absolute difference vector $m_1$.

Figure 3:
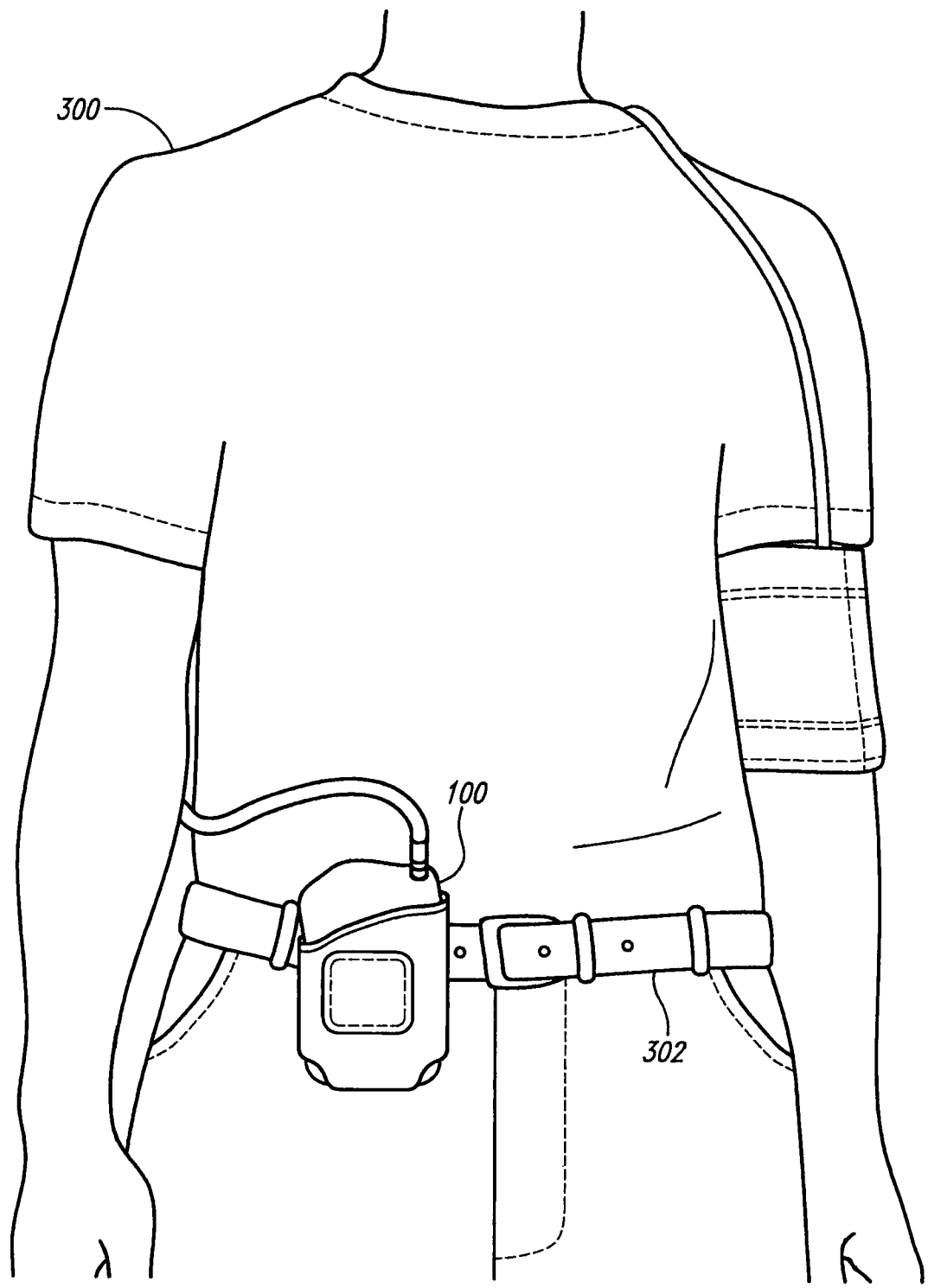
FIG. 3 shows one example of how the patient monitoring device of FIG. 1 may be attached to a patient.

FIG. 3 shows one example of how the patient monitoring device 100 may be attached to the patient. The patient monitoring device 100 needs to be attached to the patient 300 while recording physiological data so as to simultaneously record actigraphy data. Patient 300 wears the patient monitoring device 100 attached to the patient's belt 302. Alternatively, the patient monitoring device may be kept in a pocket in the patients clothing or attached to the patient via some other means.

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the invention is not limited except as by the appended claims.

The invention claimed is:

1. A patient monitoring device comprising:
   (a) a sensor interface configured to receive physiological sensor data, said sensor interface comprising an ambulatory blood pressure monitor (APBM);
   (b) an activity sensor configured to generate activity data, said activity sensor including an accelerometer; and
   (c) a processor coupled with the sensor interface and said activity sensor configured to synchronize said APBM's data and said accelerometer's data.

2. The patient monitoring device of claim 1, wherein said physiological sensor data further includes an electrocardiogram monitor with integrated actigraphy.

3. The patient monitoring device of claim 1, wherein said physiological sensor data further includes an oxygen saturation monitor with integrated actigraphy.

4. The patient monitoring device of claim 1, wherein said activity sensor is a multiple axis accelerometer.

5. The patient monitoring device of claim 1, wherein said activity sensor is a gyroscope.

6. The patient monitoring device of claim 1, wherein said activity sensor is an inclination sensor.

7. The patient monitoring device of claim 1, further comprising a memory to store the physiological sensor data including ambulatory blood pressure monitoring data and associated synchronized activity data.

8. The patient monitoring device of claim 1 wherein:
   the sensor interface is configured to receive physiological sensor data comprising a plurality of data points, each data point associated with one of a plurality of sample windows;
   said activity sensor is configured to generate activity data comprising a plurality of a summed absolute difference vectors, each summed absolute difference vector associated with one of the plurality of sample windows; and
   the processor is configured to associate the physiological sensor data with synchronized portions of activity data by associating each physiological sensor data point with one of the summed absolute difference vectors associated with the same sample window.

* * * * *